US012624072B2

(12) United States Patent
Luca et al.

(10) Patent No.: US 12,624,072 B2
(45) Date of Patent: *May 12, 2026

(54) ENGINEERING BROADLY REACTIVE HUMAN NOTCH LIGANDS AS NOVEL TOOLS FOR BIOMEDICAL APPLICATIONS

(71) Applicant: H. LEE MOFFITT CANCER CENTER AND RESEARCH INSTITUTE, INC., Tampa, FL (US)

(72) Inventors: Vincent Luca, Tampa, FL (US); David Gonzalez Perez, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 878 days.

This patent is subject to a terminal disclaimer.

(21) Appl. No.: 17/608,013

(22) PCT Filed: May 1, 2020

(86) PCT No.: PCT/US2020/030977
§ 371 (c)(1),
(2) Date: Nov. 1, 2021

(87) PCT Pub. No.: WO2020/223610
PCT Pub. Date: Nov. 5, 2020

(65) Prior Publication Data
US 2022/0348617 A1 Nov. 3, 2022

Related U.S. Application Data

(60) Provisional application No. 62/841,460, filed on May 1, 2019.

(51) Int. Cl.
| | |
|---|---|
| *C07K 14/47* | (2006.01) |
| *A61P 35/00* | (2006.01) |
| *C12N 15/10* | (2006.01) |

(52) U.S. Cl.
CPC .............. *C07K 14/47* (2013.01); *A61P 35/00* (2018.01); *C12N 15/1037* (2013.01)

(58) Field of Classification Search
None
See application file for complete search history.

(56) References Cited

U.S. PATENT DOCUMENTS

| | | | |
|---|---|---|---|
| 2003/0049788 A1* | 3/2003 | Sakano ................ | C07K 14/475 |
| | | | 435/372 |
| 2006/0204508 A1 | 9/2006 | Champion et al. | |
| 2011/0213127 A1 | 9/2011 | Gill et al. | |
| 2017/0080052 A1 | 3/2017 | Li et al. | |
| 2018/0064662 A1 | 3/2018 | Fukumura et al. | |
| 2019/0134169 A1 | 5/2019 | Zhang et al. | |

FOREIGN PATENT DOCUMENTS

| | | |
|---|---|---|
| WO | 2015008070 A1 | 1/2015 |
| WO | 2018017827 A1 | 1/2018 |
| WO | 2018178666 A1 | 10/2018 |
| WO | 2018183216 A1 | 10/2018 |
| WO | 2019106163 A1 | 6/2019 |
| WO | 2020047099 A1 | 3/2020 |

OTHER PUBLICATIONS

Costello et al. (Pancreat Disord Ther; Suppl 4; doi:10.4172/2165-7092.S4-002) (Year: 2013).*
Gharaibeh et al. (Mol Pharmacol. Nov. 2020;98(5):559-576) (Year: 2020).*
International Search Report and Written Opinion in PCT/US2020/030977. Mailed Sep. 30, 2020. 13 pages.
Luca et al. "Structural basis for Notch1 engagement of Delta-like 4" Science, Feb. 20, 2015.
Adler, S.H. et al. Notch signaling augments T cell responsiveness by enhancing CD25 expression. J.Immunol. 171, 2896-2903 (2003).
Almquist, R.G. et al. "Synthesis and biological activity of a ketomethylene analog of a tripeptide inhibitor of angiotensin converting enzyme." Journal of medicinal chemistry 23.12 (1980): 1392-1398.
Backer, R.A. et al. A central role for Notch in effector CD8(+) T cell differentiation. Nat.Immunol. 15, 1143-1151 (2014).
Bagshawe, K.D. "Towards generating cytotoxic agents at cancer sites. The First Bagshawe Lecture." Br. J. Cancer 60 (1989): 275-281.
Bagshawe, K.D. et al. "A cytotoxic agent can be generated selectively at cancer sites." British journal of cancer 58.6 (1988): 700-703.
Balkwill, F. & Mantovani, A. Inflammation and cancer: back to Virchow? Lancet 357, 539-545 (2001).
Battelli, M.G. et al. "T lymphocyte killing by a xanthine-oxidase-containing immunotoxin." Cancer Immunology, Immunotherapy 35.6 (1992): 421-425.
Benedito, R. et al. The Notch Ligands Dll4 and Jagged1 Have Opposing Effects on Angiogenesis. Cell 137, 1124-1135 (2009).
Bheeshmachar, G. et al. Evidence for a role for notch signaling in the cytokine-dependent survival of activated T cells. J.Immunol. 177, 5041-5050 (2006).
Brown, V.I. & Greene, M.I. "Molecular and cellular mechanisms of receptor-mediated endocytosis." DNA and cell biology 10.6 (1991): 399-409.

(Continued)

*Primary Examiner* — Sergio Coffa
(74) *Attorney, Agent, or Firm* — Meunier Carlin & Curfman LLC

(57) ABSTRACT

Disclosed are compositions and methods for engineered DLL4 proteins. In one aspect, disclosed herein are engineered DLL4 proteins comprising a conservative amino acid substitution at a residue corresponding to residues 28, 107, 143, 194, and 206 as set forth in SEQ ID NO: 1 and further comprising at least one conservative amino acid substitution at residues 256, 257, 271, 280, 301, and 305 as set forth in SEQ ID NO: 1.

20 Claims, 9 Drawing Sheets

Specification includes a Sequence Listing.

(56) References Cited

OTHER PUBLICATIONS

Cho, O.H. et al. Notch regulates cytolytic effector function in CD8+ T cells. J.Immunol. 182, 3380-3389 (2009).

Cordle, J. et al. A conserved face of the Jagged/Serrate DSL domain is involved in Notch trans-activation and cis-inhibition. Nat. Struct. Mol. Biol. 15, 849-857 (2008).

Creighton, Proteins: Structure and Molecular Properties, W. H. Freeman & Co., San Francisco [1983], 88.

Extended European Search Report issued for European Application No. 20837680.6, dated May 30, 2023.

Fletcher, M. et al. I-Arginine depletion blunts antitumor T-cell responses by inducing myeloid-derived suppressor cells. Cancer Res. 75, 275-283 (2015).

Guruharsha, K.G. et al. The Notch signalling system: recent insights into the complexity of a conserved pathway. Nat. Rev.Genet. 13, 654-666 (2012).

Guy, C.S. et al. Distinct TCR signaling pathways drive proliferation and cytokine production in T cells. Nat. Immunol. 14, 262-270 (2013).

Handbook of Monoclonal Antibodies, Ferrone et al., eds., Noges Publications, Park Ridge, N.J., (1985) ch. 22 and pp. 303-357.

Hann, M.M., et al. "On the double bond isostere of the peptide bond: preparation of an enkephalin analogue." Journal of the Chemical Society, Perkin Transactions 1 (1982): 307-314.

Holladay, M.W. & Rich, D.H. "Synthesis of hydroxyethylene and ketomethylene dipeptide isosteres." Tetrahedron Letters 24.41 (1983): 4401-4404.

Hruby, V.J. "Conformational restrictions of biologically active peptides via amino acid side chain groups." Life sciences 31.3 (1982): 189-199.

Hudson, D. "Matrix assisted synthetic transformations: a mosaic of diverse contributions. I. The pattern emerges." Journal of combinatorial chemistry 1.5 (1999): 333-360.

Hughes, B.J. et al. "Monoclonal antibody targeting of liposomes to mouse lung in vivo." Cancer research 49.22 (1989): 6214-6220.

International Preliminary Report on Patentability issued for Application No. PCT/US2020/041765, dated Jan. 20, 2022.

International Search Report and Written Opinion in PCT/US2020/041765. Mailed Oct. 19, 2020. 13 pages.

Intlekofer, A.M. et al. Effector and memory CD8+ T cell fate coupled by T-bet and eomesodermin. Nat.Immunol. 6, 1236-1244 (2005).

Jaeger, J.A. et al. "Improved predictions of secondary structures for RNA." Proceedings of the National Academy of Sciences 86.20 (1989): 7706-7710.

Jaeger, J.A. et al. "Predicting optimal and suboptimal secondary structure for RNA." (1990): 281-306.

Jaleco, A.C. et al. Differential Effects of Notch Ligands Delta-1 and Jagged-1 in Human Lymphoid Differentiation. J. Exp. Med. 194, 991-1002 (2001).

Jennings-White, C. & Almquist, R.G. "Synthesis of ketomethylene analogs of dipeptides." Tetrahedron Letters 23.25 (1982): 2533-2534.

Joshi, I. et al. Notch signaling mediates G1/S cell-cycle progression in T cells via cyclin D3 and its dependent kinases. Blood 113, 1689-1698 (2009).

Kelliher et al. NOTCH Signaling in T-Cell-Mediated Anti-Tumor Immunity and T-Cell-Based Immunotherapies. Frontiers in Immunology. 9:1-6(Aug. 20, 2018).

Kuijk, L. M. et al. Notch controls generation and function of human effector CD8+ T cells. Blood 121, 2638-2646 (2013).

Lehar, S. M., Dooley, J., Farr, A. G. & Bevan, M. J. Notch ligands Delta 1 and Jagged1 transmit distinct signals to T-cell precursors. Blood 105, 1440-1447 (2005).

Litzinger, D.C. & Huang, L. "Biodistribution and immunotargetability of ganglioside-stabilized dioleoylphosphatidylethanolamine liposomes." Biochimica et Biophysica Acta (BBA)-Biomembranes 1104.1 (1992): 179-187.

Liu et al. Abstract of: Identification of Domains for Efficient Notch Signaling Activity in Immobilized Notch Ligand Proteins. Journal of Cellular Biochemistry. 118:785-796(Sep. 17, 2016).

Luca, V.C. et al. Notch-Jagged complex structure implicates a catch bond in tuning ligand sensitivity. Science. 355(6331):1320-1324(2017).

Maekawa, Y. et al. Notch2 integrates signaling by the transcription factors RBP-J and CREB1 to promote T cell cytotoxicity. Nat. Immunol. 9, 1140-1147 (2008).

Maus, M.V. et al. Adoptive immunotherapy for cancer or viruses. Annu Rev Immunol 32, 189-225, doi: 10.1146/annurev-immunol-032713-120136 (2014).

Mohtashami, M. et al. Direct comparison of DII1-and DII4-mediated Notch activation levels shows differential lymphomyeloid lineage commitment outcomes. J. Immunol. Baltim. Md 1950 185, 867-876 (2010).

Morley, J.S. "Modulation of the action of regulatory peptides by structural modification." Trends in Pharmacological Sciences 1.2 (1980): 463-468.

Needleman, S.B. & Wunsch, C.D. "A general method applicable to the search for similarities in the amino acid sequence of two proteins." Journal of molecular biology 48.3 (1970): 443-453.

Nowell, et al. Notch as a tumour suppresor. Nat Rev Cancer. 17(3):145-159(2017).

Palaga, T. et al. TCR-mediated Notch signaling regulates proliferation and IFN-gamma production in peripheral T cells. J.Immunol. 171, 3019-3024 (2003).

Pearson, W.R. & Lipman, D.J. "Improved tools for biological sequence comparison." Proceedings of the National Academy of Sciences 85.8 (1988): 2444-2448.

Perales-Puchalt, A. et al. Follicle-Stimulating Hormone Receptor Is Expressed by Most Ovarian Cancer Subtypes and Is a Safe and Effective Immunotherapeutic Target. Clin Cancer Res 23, 441-453, doi: 10.1158/1078-0432.CCR-16-0492 (2017).

Pietersz, G.A. & Mckenzie, I.F.C. "Antibody conjugates for the treatment of cancer." Immunological reviews 129.1 (1992): 57-80.

Raber, P.L. et al. T cells conditioned with MDSC show an increased anti-tumor activity after adoptive T cell based immunotherapy. Oncotarget 7, 17565-17578, doi:10.18632/oncotarget.8197 (2016).

Radtke, F. et al. Notch signaling in the immune system. Immunity. 32, 14-27 (2010).

Radtke, F. et al. Regulation of innate and adaptive immunity by Notch. Nat.Rev.Immunol. 13, 427-437 (2013).

Rodriguez, P.C. et al. Arginase I in myeloid suppressor cells is induced by COX-2 in lung carcinoma. J.Exp.Med. 202, 931-939 (2005).

Rodriguez, P.C. et al. Arginase I production in the tumor microenvironment by mature myeloid cells inhibits T-cell receptor expression and antigen-specific T-cell responses. Cancer Res. 64, 5839-5849 (2004).

Rodriguez, P.C. et al. Arginase I-producing myeloid-derived suppressor cells in renal cell carcinoma are a subpopulation of activated granulocytes. Cancer Res. 69, 1553-1560 (2009).

Rodriguez, P.C. et al. L-arginine deprivation regulates cyclin D3 mRNA stability in human T cells by controlling HuR expression. J.Immunol. 185, 5198-5204 (2010).

Rodriguez, P.C. et al. L-arginine availability regulates T-lymphocyte cell-cycle progression. Blood 109, 1568-1573 (2007).

Roffler, S.R. et al. "Anti-neoplastic glucuronide prodrug treatment of human tumor cells targeted with a monoclonal antibody-enzyme conjugate." Biochemical pharmacology 42.10 (1991): 2062-2065.

Sadelain, M. et al. Therapeutic T cell engineering. Nature 545, 423-431, doi:10.1038/nature22395 (2017).

Schaller et al. "Delta-like 4 differentially regulates murine CD4+ T cell expansion via BMI1," PLoS One, vol. 5, No. 8, Jan. 1, 2010, p. e12172, DOI: 10.1371/journal.pone.0012172.

Schmitt, T.M. et al. Maintenance of T Cell Specification and Differentiation Requires Recurrent Notch Receptor-Ligand Interactions. J. Exp. Med. 200, 469-479 (2004).

Senter, P.D. et al. "Generation of 5-fluorouracil from 5-fluorocytosine by monoclonal antibody-cytosine deaminase conjugates." Bioconjugate chemistry 2.6 (1991): 447-451.

Senter, P.D. et al. "Generation of cytotoxic agents by targeted enzymes." Bioconjugate chemistry 4.1 (1993): 3-9.

(56)     References Cited

OTHER PUBLICATIONS

Sierra, R.A. et al. Anti-Jagged Immunotherapy Inhibits MDSCs and Overcomes Tumor-Induced Tolerance. Cancer Res 77, 5628-5638, doi:10.1158/0008-5472.CAN-17-0357 (2017).

Sierra, R.A. et al. Rescue of notch-1 signaling in antigen-specific CD8+ T cells overcomes tumor-induced T-cell suppression and enhances immunotherapy in cancer. Cancer Immunol. Res. 2, 800-811 (2014).

Smith et al. Antibodies in Human Diagnosis and Therapy, Haber et al., eds., Raven Press, New York (1977) pp. 365-389.

Smith, T.F. & Waterman, M.S. "Comparison of biosequences." Advances in applied mathematics 2.4 (1981): 482-489.

Spatola, A.F. et al. "Structure-activity relationships of enkephalins containing serially replaced thiomethylene amide bond surrogates." Life Sciences 38.14 (1986): 1243-1249.

Sprinzak, D. et al. Cis-interactions between Notch and Delta generate mutually exclusive signalling states. Nature 465, 86-90 (2010).

Supplementary Materials from Science 347(6224) 25 pages, published Feb. 20, 2015.

Thevenot, P.T. et al. The stress-response sensor chop regulates the function and accumulation of myeloid-derived suppressor cells in tumors. Immunity. 41, 389-401 (2014).

Varnum-Finney, B. et al. Immobilization of Notch ligand, Delta-1, is required for induction of notch signaling. J. Cell Sci. 113 Pt 23, 4313-4318 (2000).

Wang, X. & Ha, T. Defining Single Molecular Forces Required to Activate Integrin and Notch Signaling. Science 340, 991-994 (2013).

Zuker, M. "On finding all suboptimal foldings of an RNA molecule." Science 244.4900 (1989): 48-52.

* cited by examiner

FIG. 3C hDLL4 or DLL4 variant

*Sensor chip*

Notch1, Notch2, or Notch3
(ligand-binding domains)

Equilibrium dissociation constants (nM)

| Ligand (N-EGF3) | hNotch1 (EGF6-13) | hNotch2 (EGF6-13) | hNotch 3 (EGF6-13) |
|---|---|---|---|
| hDLL4 | 17,900 | 35,700 | 22,200 |
| hDLL4 site2 | 471 | 3,250 | 1,650 |
| hDLL4 E12 | 103 | 244 | 122 |
| DLL4.v3 | 20.0 | 31.4 | 27.3 |

Fold increase in affinity relative to WT DLL4

| Ligand (N-EGF3) | hNotch1 (EGF6-13) | hNotch2 (EGF6-13) | hNotch 3 (EGF6-13) |
|---|---|---|---|
| hDLL4 site 2 | 38.0 | 11.0 | 13.3 |
| hDLL4 E12 | 173 | 146.3 | 182 |
| DLL4.v3 | 895 | 1137 | 813 |

ENGINEERING BROADLY REACTIVE HUMAN NOTCH LIGANDS AS NOVEL TOOLS FOR BIOMEDICAL APPLICATIONS

This application is a United States National Phase Patent Application of International Patent Application Number PCT/US2020/030977, filed on May 1, 2020, which claims the benefit of U.S. Provisional Application No. 62/841,460, filed on May 1, 2019, applications which are incorporated herein by reference in their entireties.

This invention was made with government support under Grant No. CA204738 awarded by the National Institutes of Health. The government has certain right in the invention.

I. BACKGROUND

The Notch pathway plays a central role in cellular homeostasis, embryonic development and stem cell renewal. Despite Notch receptors and ligands being major emerging targets for cancer therapeutics, the intrinsically low binding affinity between Delta-like (DLL) or Jagged (Jag) ligands and Notch receptors limits the utility of these molecules in biomedical applications. What are needed are new therapeutics and ligands that have enhanced affinity for multiple human Notch receptors.

II. SUMMARY

Disclosed are methods and compositions related to engineered DLL4 proteins.

In one aspect, disclosed herein are engineered DLL4 proteins comprising a conservative amino acid substitution at a residue corresponding to residues 28, 107, 143, 194, and 206 as set forth in SEQ ID NO: 1 and further comprising at least one conservative amino acid substitution at residues 256, 257, 271, 280, 301, and 305 as set forth in SEQ ID NO: 1.

Also disclosed herein are engineered DLL4 protein of any preceding aspect, wherein the substitution at residue 28 comprises a glysine to serine substitution (G28S).

In one aspect, disclosed herein are engineered DLL4 protein of any preceding aspect, wherein the substitution at residue 107 comprises a phenylalanine to leucine substitution (F107L).

Also disclosed herein are engineered DLL4 protein of any preceding aspect, wherein the substitution at residue 143 comprises a isoleucine to phenylalanine substitution (I143F).

In one aspect, disclosed herein are engineered DLL4 protein of any preceding aspect, wherein the substitution at residue 194 comprises a histidine to tyrosine substitution (H194Y).

Also disclosed herein are engineered DLL4 protein of any preceding aspect, wherein wherein the substitution at residue 206 comprises a leucine to proline substitution (L206P).

In one aspect, disclosed herein are engineered DLL4 proteins of any preceding aspect, wherein the amino acid at residue 256 comprises a histidine, tyrosine, phenylalanine, leucine, asparagine, isoleucine, valine, or aspartic acid (such as, for example, a H256Y substitution, H256F substitution, H256L substitution. H256N substitution, H256I substitution, H256V substitution, or H256D substitution).

Also disclosed herein are engineered DLL4 proteins of any preceding aspect, wherein the amino acid at residue 257 comprises a proline, histidine, leucine, isoleucine, threonine, asparagine, tyrosine, serine, or phenylalanine (such as, for example, a N257P substitution, N257H substitution, N257L substitution, N257I substitution, N257T substitution, N257Y substitution, N257S substitution, or N257F substitution).

In one aspect, disclosed herein are engineered DLL4 proteins of any preceding aspect, wherein the amino acid at residue 271 comprises a leucine, proline, histidine, asparagine, threonine, or isoleucine (such as, for example, a T271L substitution, T271P substitution, T271H substitution, T271N substitution, or T271I substitution).

Also disclosed herein are engineered DLL4 proteins of any preceding aspect, wherein the amino acid at residue 280 comprises a phenylalanine, leucine, tyrosine, or histidine (F280Y substitution, F280L substitution, or F280H substitution).

In one aspect, disclosed herein are engineered DLL4 proteins of any preceding aspect, wherein the amino acid at residue 301 comprises a serine, asparagine, arginine, or histidine (S301H substitution, S301N substitution, or S301R substitution).

Also disclosed herein are engineered DLL4 proteins of any preceding aspect, wherein the amino acid at residue 305 comprises a glutamine, proline, arginine, or leucine (Q305P substitution, Q305R substitution, or Q305L substitution).

In one aspect, disclosed herein are engineered DLL4 proteins of any preceding aspect, wherein DLL4 protein comprises SEQ ID NO: 3 or SEQ ID NO: 4.

Also disclosed herein are methods of treating, inhibiting, reducing, decreasing, ameliorating, and/or preventing a cancer and/or metastasis comprising in a subject administering to the subject any of the engineered DLL4 proteins of any preceding aspect.

In one aspect, disclosed herein are antibodies that bind to any of the engineered DLL4 proteins of any preceding aspect.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 3A shows the engineering strategy to create a "second" binding site in DLL4 based on Notch-Jagged crystal structure.

FIG. 3B shows highlighted the positions subjected to mutagenesis.

FIG. 3C show a representation of the structural similarity between DLL4 and Jagged1 structures.

3

Figures 5A, 5B:
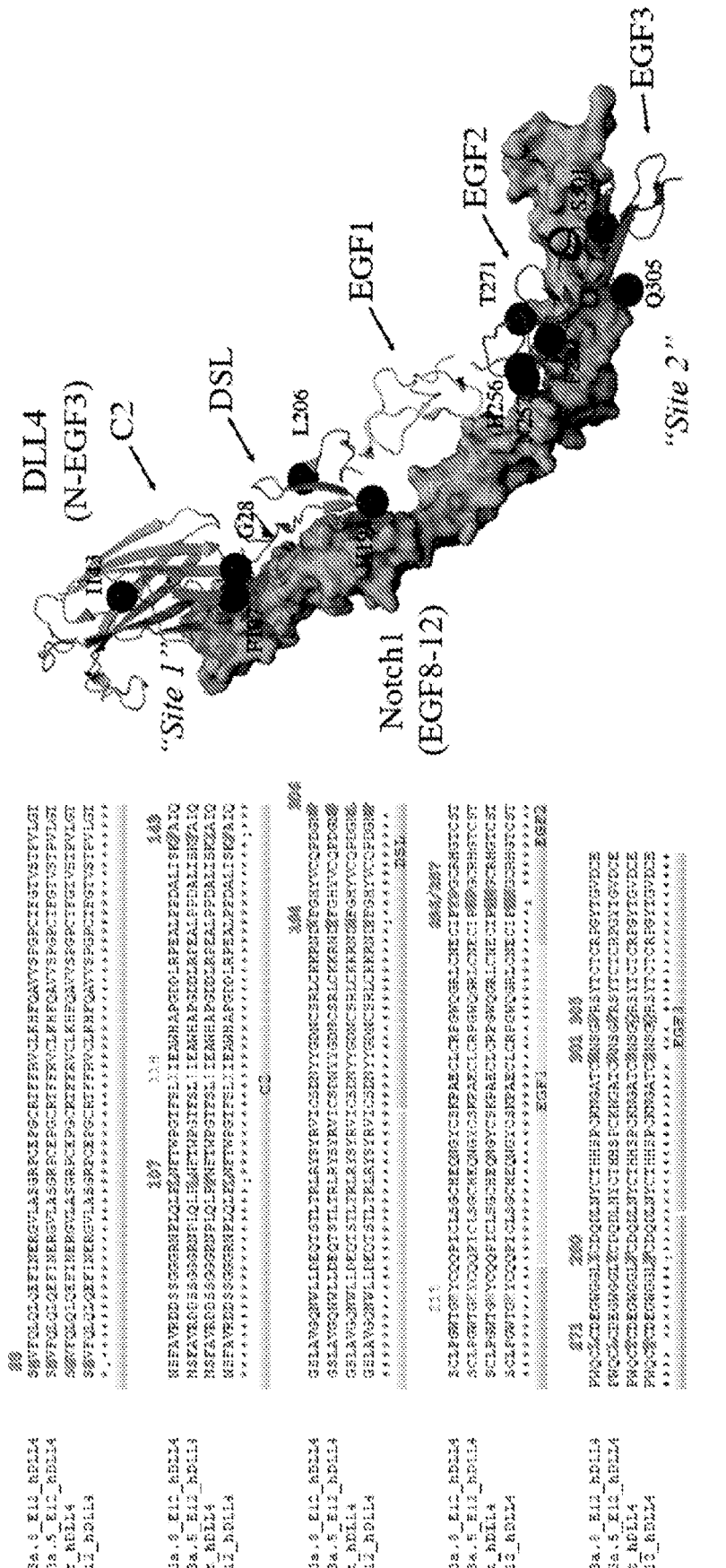
FIG. 5A shows a multiple sequence alignment of wild-type DLL4, humanized E12 DLL4 and combo mutants obtained after mutations transfer with rat E12 mutations.

FIG. 5B shows a highlighted structure of Notch1 and DLL4 (protein complex model) showing the positions of the new mutations involved in the "site 1" and "site 2" of Notch binding interface.

Figures 6A, 6B:
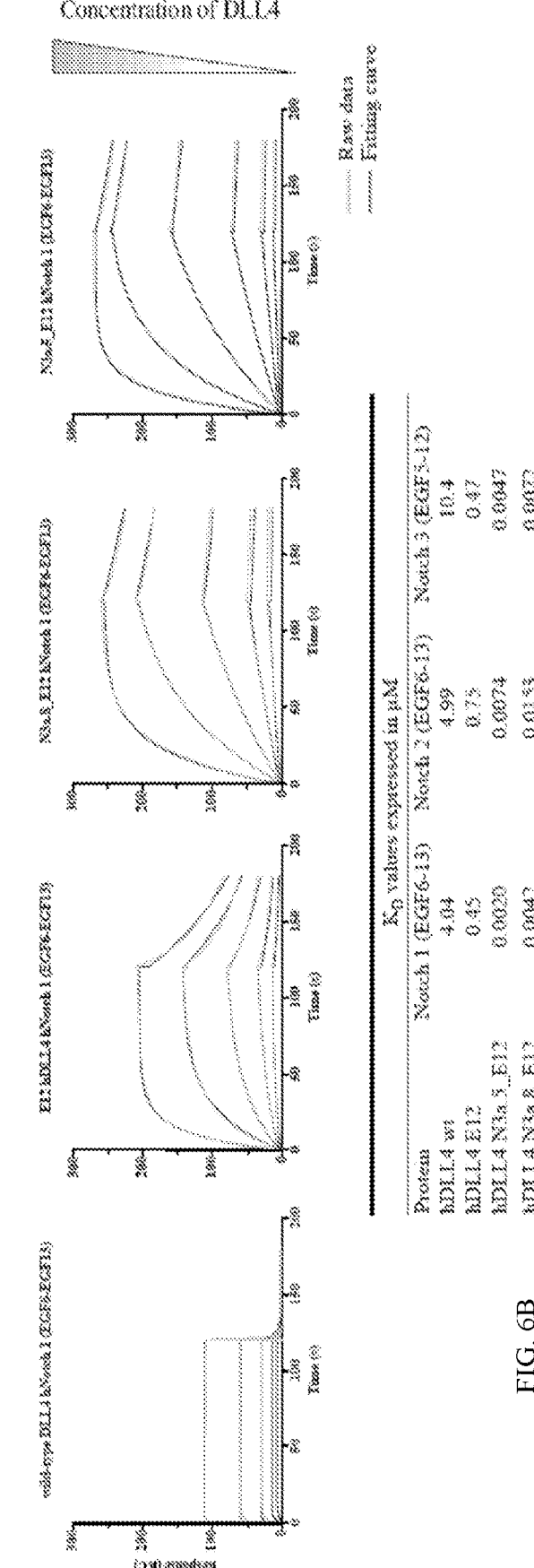

FIG. 6A shows the plots obtained by SPR with wild-type DLL4, humanized E12 DLL4, N3a.5_E12 and N3a.8_E12 combo mutants binding to Notch 1. The black lines indicate raw data and the red solid lines show the fitting of the data to an association-then-dissociation model.

FIG. 6B indicates the dissociation constants of the wild-type, E12 and combo mutants for Notch 1, Notch 2 and Notch 3.

Figure 7:
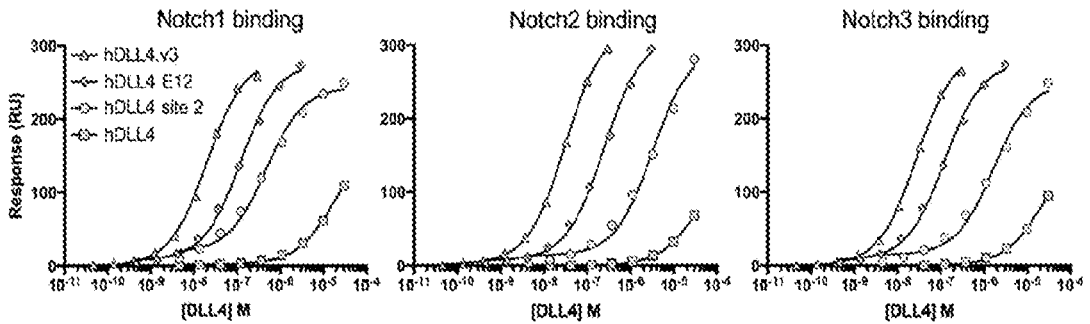
Figure 7:
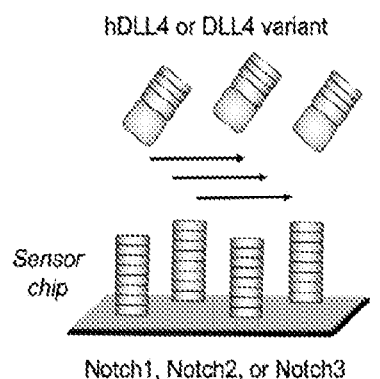

FIG. 7 shows Binding affinities between DLL4 variants and Notch receptor subtypes as determined by surface plasmon resonance (SPR).

Figure 8:
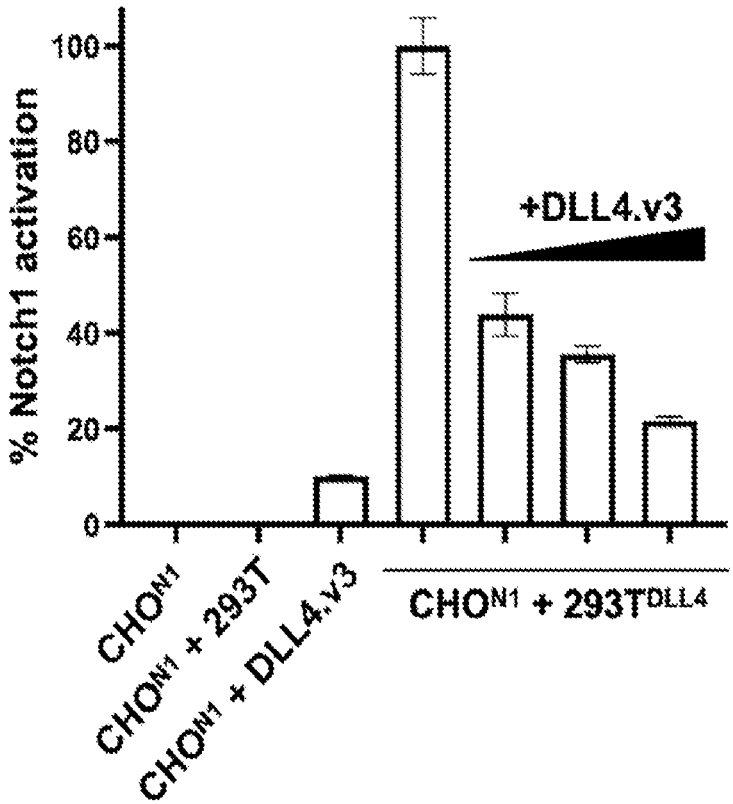

FIG. 8 shows high-affinity DLL4 variant inhibits Notch signaling.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

"Treat," "treating," "treatment," and grammatical variations thereof as used herein, include the administration of a composition with the intent or purpose of partially or completely delaying, curing, healing, alleviating, relieving, altering, remedying, ameliorating, improving, stabilizing, mitigating, and/or reducing the intensity or frequency of one or more diseases or conditions, a symptom of a disease or condition, or an underlying cause of a disease or condition. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular engineered DLL4 protein is disclosed and discussed and a number of modifications that can be made to a number of molecules including the engineered DLL4 protein are discussed, specifically contemplated is each and every combination and permutation of engineered DLL4 protein and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The Notch pathway plays a central role in cellular homeostasis, embryonic development and stem cell renewal. Notch receptors and ligands are major emerging targets for cancer drugs; however, the intrinsically low binding affinity between DLL or Jag and Notch receptors limits the utility of these ligands in biomedical applications. To overcome this barrier, structure-guided directed evolution was used to engineer a repertoire of Delta-like 4 (DLL4) ligands with greatly enhanced affinity for multiple human Notch receptors.

Using the crystal structure of a Notch receptor-ligand complex as a template, putative hot-spot residues were identified that could be mutated to enhance Notch-DLL4 binding affinity. Conservative mutations were introduced at the hot-spot positions to develop a DLL4 mutant library. Variants created were displayed on the surface of yeast and high-affinity binders were isolated over several rounds of selection by magnetic- and fluorescence-activated cell sorting. Finally, a fluorescence-based binding assay was used to determine the EC50 values of various DLL4 variants for each human Notch receptor subtype (Notch1-4).

DLL4 was affinity matured using a structure-guided mutant library that varied 9 potential contact residues within the Notch-binding site. After performing several rounds of selection against Notch 1 and Notch 3, two variants were isolated that contain several mutations in the DLL4 EGF2 and EGF3 domains. Both human DLL4 variants were further modified to incorporate 5 additional mutations derived from a previously reported high-affinity rat DLL4 variant. The final chimeric proteins exhibited greatly increased binding relative to wild-type DLL4, with binding EC50 values decreasing from the micromolar range to the low nanomolar range. Additionally, it was determined that the newly generated DLL4 ligands had enhanced affinity for Notch1-4, indicating that they have the potential to function as broadly reactive "pan-Notch" activators.

In one aspect, disclosed herein are engineered DLL4 proteins comprising a conservative amino acid substitution at a residue corresponding to residues 28, 107, 143, 194, and 206 as set forth in SEQ ID NO: 1 and further comprising at least one conservative amino acid substitution at residues 256, 257, 271, 280, 301, and 305 as set forth in SEQ ID NO: 1. For example, the substitution of the engineered DLL4 protein can comprise a glysine to swine substitution at residue 28 (G28S), a phenylalanine to leucine substitution at residue 107 (F107L), an isoleucine to phenylalanine substitution at residue 143 (I143F), a histidine to tyrosine substitution at residue 194 (H194Y), and a leucine to proline substitution at residue 206 (L206P).

As noted above, the engineered DLL4 proteins can comprise one, two, three, four, five, or six substitutions at residues 256, 257, 271, 280, 301, and 305 as set forth in SEQ ID NO: 1. Thus, it is understood and herein contemplated that any one, or combination of any of the residues 256, 257, 271, 280, 301, and 305 can comprise a native residue or substitution. Accordingly, in one aspect, disclosed herein are engineered DLL4 proteins wherein the amino acid at residue 256 comprises a histidine, tyrosine, phenylalanine, leucine, asparagine, isoleucine, valine, or aspartic acid. For example, the amino acid at residue 256 can comprise a histidine or a substitution from histidine in wild-type (WT) human DLL4 (as set forth in SEQ ID NO: 3) to a tyrosine (a H256Y substitution) to a phenylalanine (a H256F substitution), a leucine (a H256L substitution), an asparagine (a H256N substitution), a isoleucine (a H256I substitution), a valine (a H256V substitution), or aspartic acid (a H256D substitution). Similarly, the engineered DLL4 proteins can comprise a proline, histidine, leucine, isoleucine, threonine, asparagine, tyrosine, serine, or phenylalanine at residue 257. Thus, in one aspect, the engineered DLL4 protein can comprise an asparagine at residue 257 or substitution from the asparagine in wild-type (WT) human DLL4 (as set forth in SEQ ID NO: 3) to a tyrosine (a H257Y substitution), a proline (a N257P substitution), a histidine (a N257H substitution), a leucine (a N257L substitution), an isoleucine (a N257I substitution), a threonine (a N257T substitution), a serine (a N257S substitution), or a phenylalanine (a N257F substitution). In one aspect, disclosed herein are engineered DLL4 proteins wherein the amino acid at residue 271 comprises a leucine, proline, histidine, asparagine, threonine, or isoleucine (such as, for example, a wild-type residue as set forth in SEQ ID NO: 1 (i.e., the threonine) or a substitution of the threonine for a leucine (a T271L substitution), a threonine to proline substitution (a T271P substitution), a threonine to histidine substitution (a T271H substitution), a threonine to arginine substitution (a T271N substitution), or a threonine to iso-leucine substitution (a T271I substitution). Also disclosed herein are engineered DLL4 proteins, wherein the amino acid at residue 280 comprises a phenylalanine or a substitution of the phenylalanine with a leucine (a F280L substitution), a tyrosine (a F280Y substitution), or histidine (a F280H substitution). Additionally, in one aspect, the disclosed engineered DLL4 proteins can comprise the native serine amino acid at residue 301 as set forth in SEQ ID NO: 1 or comprise a substitution of the serine for an asparagine (a S301N substitution), arginine (a S301R substitution), or a histidine (a S301H substitution). Also disclosed herein are engineered DLL4 proteins, wherein the amino acid at residue 305 comprises a glutamine, proline, arginine, or leucine and thus can comprise the wild-type amino acid as set forth in SEQ ID NO: 1 (i.e., a glutamine) or a substitution of the glutamine for a proline (a Q305P substitution), a substitution of the glutamine for an arginine (a Q305R substitution), or a substitution of the glutamine for a leucine (a Q305L substitution). In one aspect, disclosed herein are engineered DLL4 proteins of any preceding aspect, wherein DLL4 protein comprises SEQ ID NO: 3 or SEQ ID NO: 4.

It is understood and herein contemplated that Notch antagonists can be used as treatments for cancer and the disclosed DLL4 proteins operate as Notch signaling antagonists in soluble form. Accordingly, disclosed herein are methods of treating a cancer in a subject comprising administering to the subject any of the engineered DLL4 proteins disclosed herein. Furthermore, it is understood and herein contemplated that when anchored to a surface or substrate the disclosed DLL4 proteins become Notch agonists and can thus, activate Notch signaling in cells with which they come into contact. This can be useful in the activation of Notch on cells undergoing adoptive transfer such as, for example, stem cells, chimeric antigen receptor (CAR) T cells, tumor infiltrating lymphocytes (TILs) and TCR T cells. Thus, in one aspect disclosed herein are methods of activating Notch signaling in cell used in an adoptive transfer cell comprising contacting the cell any of the engineered DLL4 proteins; wherein the adoptively transferred cell comprises a stem cell, chimeric antigen (CAR) T cell, tumor infiltrating lymphocyte (TIL), or TCR T; and wherein the engineered DLL4 protein is anchored to a solid surface or substrate.

1. Homology/Identity

It is understood that one way to define any known variants and derivatives or those that might arise, of the disclosed genes and proteins herein is through defining the variants and derivatives in terms of homology to specific known sequences. For example, SE QID NO: 1 sets forth a particular sequence of an wild-type human DLL4 protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

2. Peptides a) Protein Variants

As discussed herein there are numerous variants of the DLL4 protein are known and herein contemplated. In addition, to the known functional DLL4 strain variants there are derivatives of the DLL4 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions

| Original Residue | Exemplary Conservative Substitutions, others are known in the art. |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/ identity to specific known sequences. For example, SEQ ID NO: 1 sets forth a particular sequence of human wild-type DLL4 and SEQ ID NOs: 2, 3, and 4 sets forth a particular sequence of a engineered DLL4 proteins. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include CH$_2$NH—, —CH$_2$S—, —CH$_2$—CH$_2$, —CH═CH— (cis and trans), —COCH$_2$, —CH(OH) CH$_2$—, and —CHH$_2$SO— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—CH$_2$NH—, CH$_2$CH$_2$—); Spatola et al. *Life Sci* 38:1243-1249 (1986) (—CHH$_2$—S); Hann *J. Chem. Soc Perkin Trans. I* 307-314 (1982) (—CH—CH—, cis and trans); Almquist et al. *J. Med. Chem.* 23:1392-1398 (1980) (—COCH$_2$—); Jennings-White et al. *Tetrahedron Lett* 23:2533 (1982) (—COCH$_2$—); Szelke et al. European Appln, EP 45665 CA (1982): 97:39405 (1982) (—CH(OH) CH$_2$—); Holladay et al. *Tetrahedron. Lett* 24:4401-4404 (1983) (—C(OH)CH$_2$—); and Hruby *Life Sci* 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

3. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., Br. J. Cancer, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies,* Ferrone et al., eds., Noges Publications, Park Ridge, N.J., (1985) ch. 22 and pp. 303-357; Smith et al., *Antibodies in Human Diagnosis and Therapy,* Haber et al., eds., Raven Press, New York (1977) pp. 365-389. A typical daily dosage of the antibody used alone might range from about 1 pig/kg to up to 100 mg/kg of body weight or more per day, depending on the factors mentioned above.

C. Methods of Treating a Cancer or Precancerous Syndrome

As noted herein, Notch signaling following DLL4 binding is an important interaction for tumor angiogenesis. Blocking this interaction or the resultant signaling is an important mechanism for inhibiting tumor formation and growth. In one aspect, it is understood and herein contemplated that the engineered DLL4 proteins disclosed herein can bind to Notch with greater affinity than wildtype DLL4 and also result in reduced/inhibited or no Notch signaling as a result of their binding. Thus, the engineered DLL4 proteins disclosed herein can serve as cancer therapeutics. Additionally, some of the engineered DLL4 proteins disclosed herein with higher affinity binding to Notch but without reduced signaling can serve as targets for antibodies that inhibit the interaction of DLL4 and Notch. Thus, in one aspect, disclosed herein are methods of treating, inhibiting, reducing, decreasing, ameliorating, and/or preventing a cancer and/or metastasis in a subject comprising administering to the subject any of the engineered DLL4 proteins disclosed herein. For example, disclosed herein are methods of treating, inhibiting, reducing, decreasing, ameliorating, and/or preventing a cancer and/or metastasis in a subject comprising administering to the subject an engineered DLL4 protein comprising one, two, three, four, five, or six substitutions at residues 256, 257, 271, 280, 301, and 305 as set forth in SEQ ID NO: 1 (such as, for example, an engineered DLL4 protein comprising including, but not limited to a G28S, F107L, I143F, H194Y, L206P, H256Y, H256F, H256L, H256N, H256I, H256V, H256D, N257P, N257H, N257L, N257I, N257T, N257Y, N257S, N257F, T271L, T271P, T271H, T271N, T271I, F280Y, F280L, F280H, S301H, S301N, S301R, Q305P, Q305R. and/or Q305L substitution including, but not limited to DLL4 proteins as set forth in SEQ ID NO 3 or SEQ ID NO: 4). Thus, in one aspect, disclosed herein are methods of treating, inhibiting, reducing, decreasing, ameliorating, and/or preventing a cancer and/or metastasis in a subject comprising administering to the subject an engineered DLL4 protein comprising one, two, three, four, five, or six substitutions at residues 256, 257, 271, 280, 301, and 305 as set forth in SEQ ID NO: 1 including, but not limited to engineered DLL4 proteins wherein the amino acid at residue 256 comprises a histidine as set forth in SEQ ID NO: 1 or a substitution to a tyrosine (a H256Y substitution), a phenylalanine (a H256F substitution), a leucine (a H256L substitution), an asparagine (a H256N substitution), a iso-leucine (a H256I substitution), a valine (a H256V substitution), or aspartic acid (a H256D substitution); an asparagine at residue 257 as set forth in SEQ ID NO: 1 or substitution to a tyrosine (a H257Y substitution), a proline (a N257P substitution), a histidine (a N257H substitution), a leucine (a N257L substitution), an isoleucine (a N257I substitution), a threonine (a N257T substitution), a serine (a N257S substitution), or a phenylalanine (a N257F substitution); a threonine at residue 271 as set forth in SEQ ID NO: 1 or a substitution of the threonine for a leucine (a T271L substitution), a threonine to proline substitution (a T271P substitution), a threonine to histidine substitution (a T271H substitution), a threonine to arginine substitution (a T271N substitution), or a threonine to isoleucine substitution (a T271I substitution); a phenylalanine at residue 280 as set forth in SEQ ID NO: 1 or a substitution of the phenylalanine with a leucine (a F280L substitution), a tyrosine (a F280Y substitution), or histidine (a F280H substitution); a serine amino acid at residue 301 as set forth in SEQ ID NO: 1 or a substitution of the serine for an asparagine (a S301N substitution), arginine (a S301R substitution), or a histidine (a S301H substitution); a glutamine at residue 305 as set forth in SEQ ID NO: 1 or a substitution of the glutamine for a proline (a Q305P substitution), a substitution of the glutamine for an arginine (a Q305R substitution), or a substitution of the glutamine for a leucine (a Q305L substitution)).

The disclosed methods of treating, inhibiting, reducing, decreasing, ameliorating, and/or preventing a cancer and/or metastasis comprising administering any of the engineered DLL4 proteins disclosed herein can be used to treat, reduce, inhibit, ameliorate, and/or prevent any disease where uncontrolled cellular proliferation occurs such as cancers and/or metastasis. A representative but non-limiting list of cancers that the disclosed compositions can be used to treat is the following: Myelodysplastic Syndrome (MDS), lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

It is understood and herein contemplated that the disclosed methods of treating, preventing, inhibiting, ameliorating, and/or reducing a cancer and/or metastasis in a subject comprising administering any of the engineered DLL4 proteins disclosed herein can further comprise the administration of any anti-cancer agent that would further aid in the reduction, inhibition, treatment, and/or elimination of the cancer or metastasis (such as, for example, gemcitabine). Anti-cancer agents that can be used in the disclosed bioresponsive hydrogels or as an additional therapeutic agent in addition to the disclosed pharmaceutical compositions, and/or bioresponsive hydrogel matrixes for the methods of reducing, inhibiting, treating, ameliorating, decreasing, preventing, and/or eliminating a cancer and/or metastasis in a subject disclosed herein can comprise any anti-cancer agent known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EP-OCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab, Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 1:
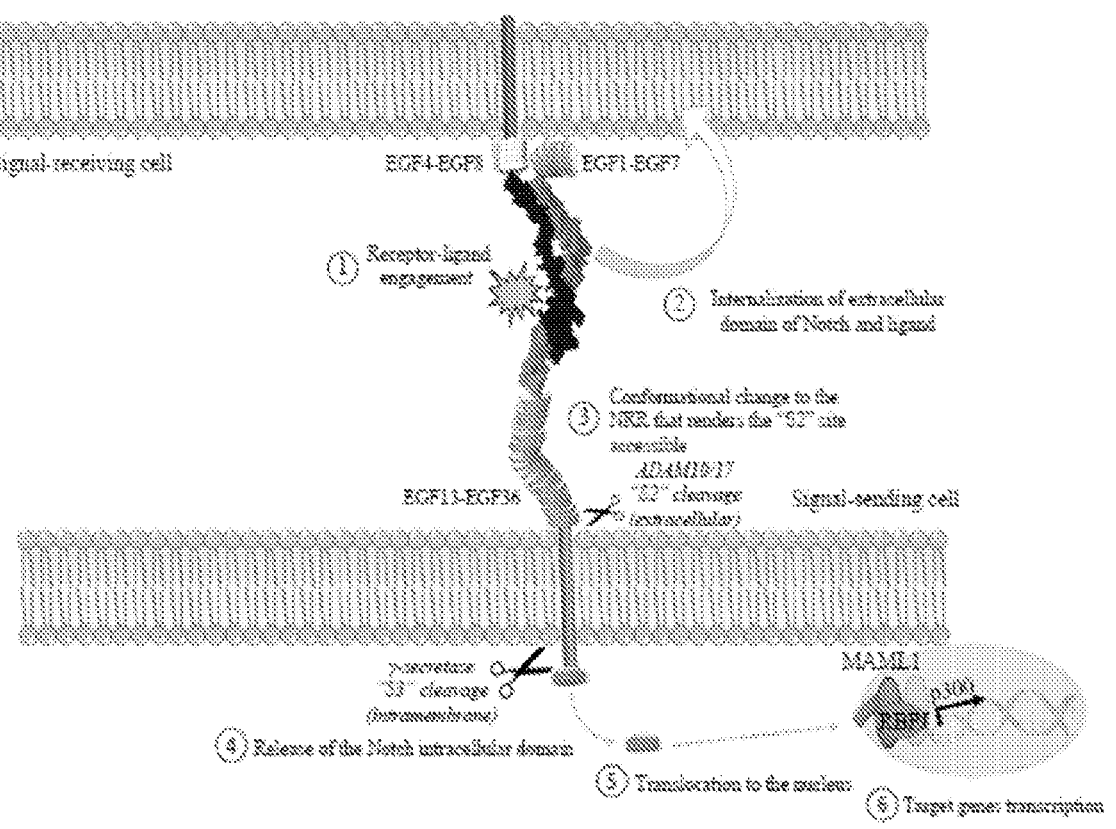
FIG. 1 shows the canonical NOTCH signal mechanism after ligand engagement with DLL or Jag.
Figure 2:
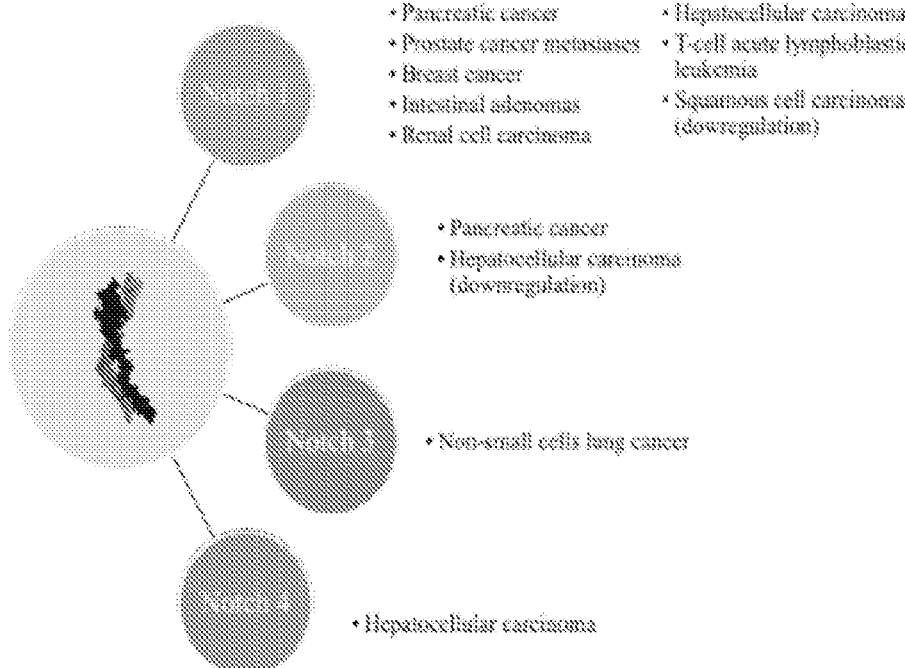
FIG. 2 shows that NOTCH signaling is an important target for cancer therapy.
Figure 4A:
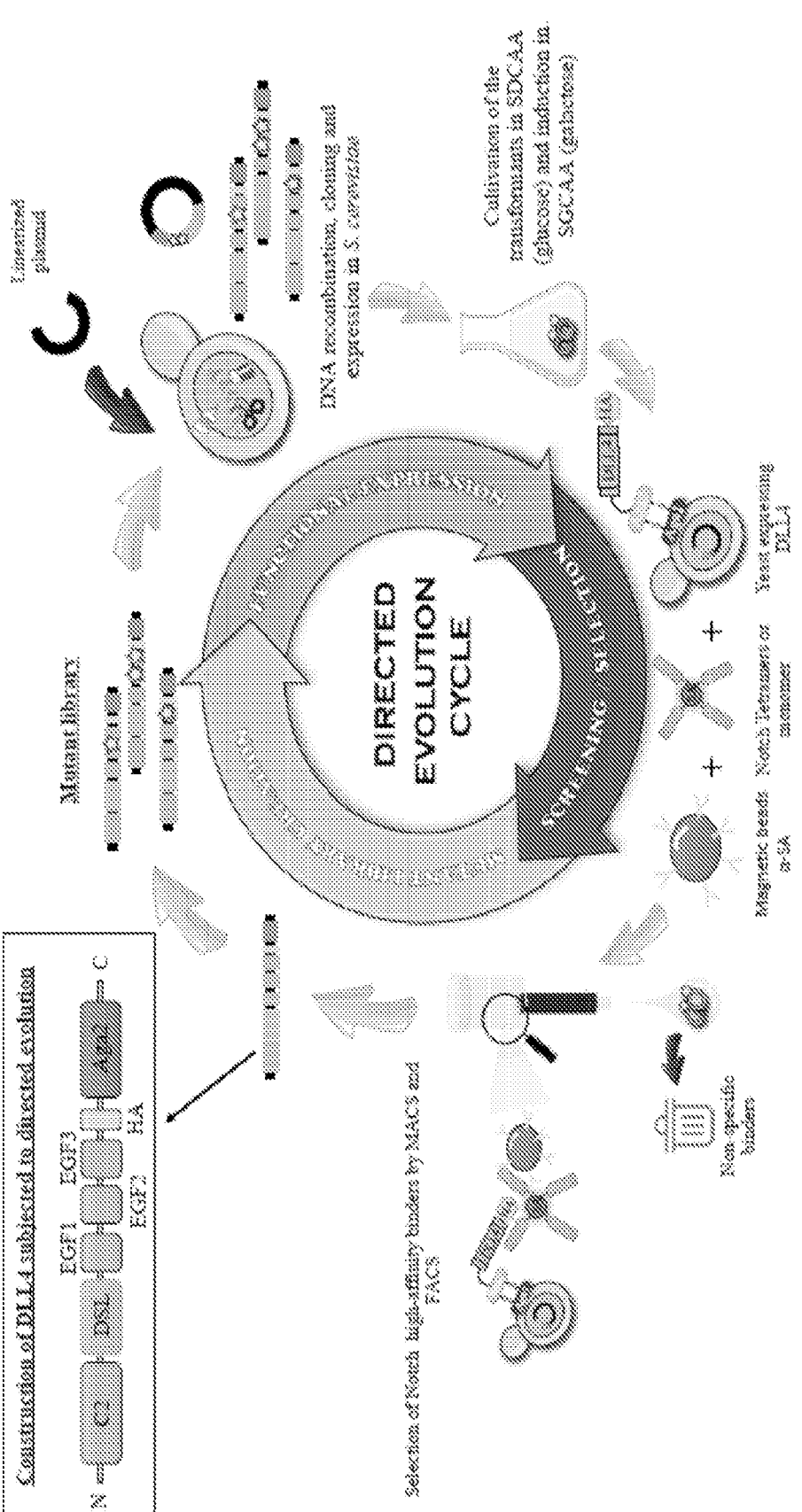
FIG. 4A shows a schematic view of the directed evolution processed followed for human DLL4 selections.
Figures 4B, 4C, 4D:
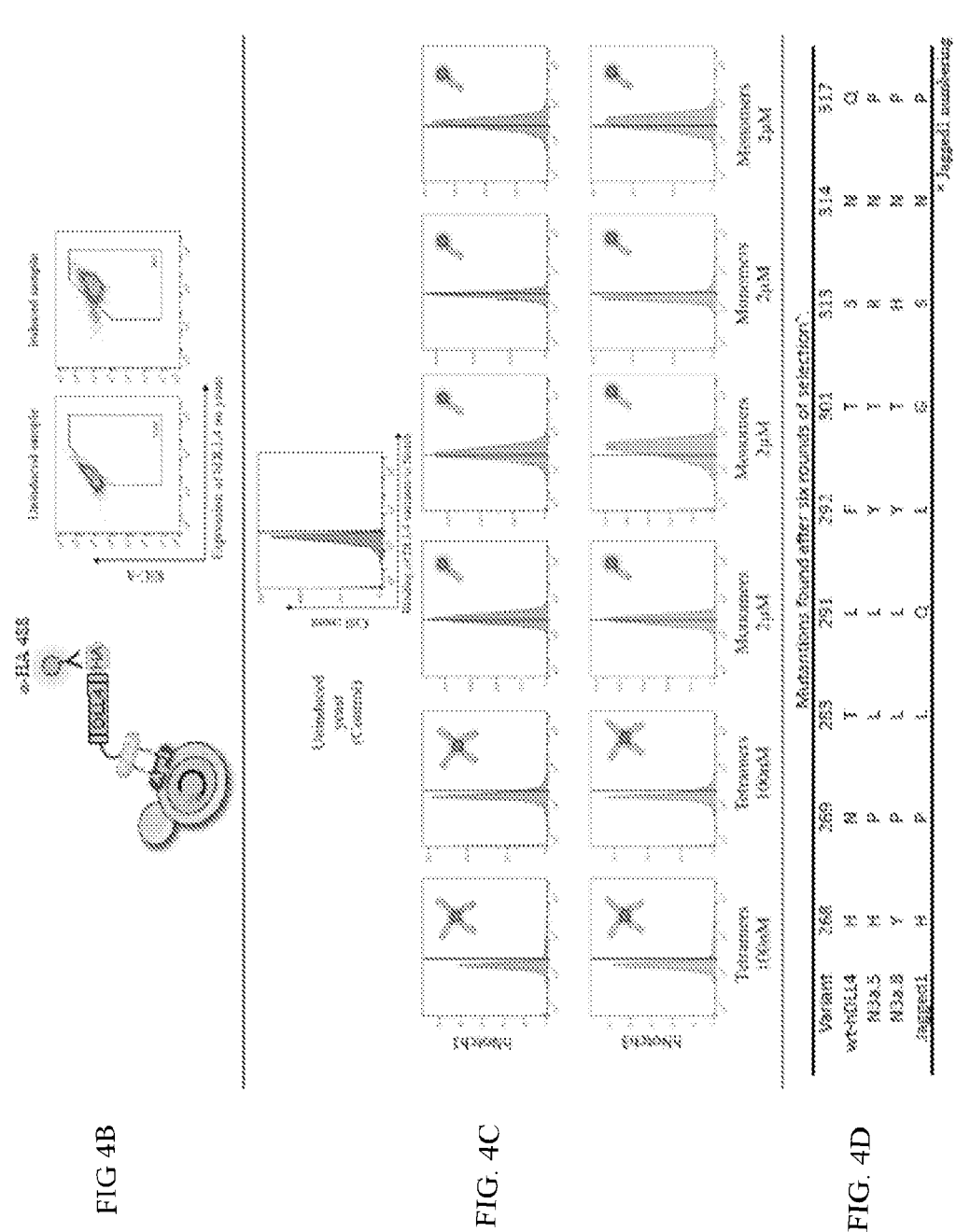
FIG. 4B shows the detection of DLL4 expression on yeast surface through HA epitope.
FIG. 4C shows the histogram obtained after sorting the yeast population selected with tetramers/monomers.
FIG. 4D shows the mutations found in the two new variants compared with wild-type DLL4 and Jagged1 sequences.

The Notch pathway plays a central role in cellular homeostasis, embryonic development and stem cell renewal (FIG. 1). The upregulation or downregulation of Notch signaling influences many different types of cancer (FIG. 2). Therefore, the application of high-affinity ligands for Notch-dependent therapy is very exciting because these ligands could work not only as Notch activators (presented on cell surfaces), but also as Notch signaling inhibitors (in soluble form). Accordingly, Notch receptors and ligands are major emerging targets for cancer drugs; however, the intrinsically low binding affinity between DLL or Jag and Notch receptors limits the utility of these ligands in biomedical applications. To overcome this barrier, structure-guided directed evolution was used to engineer a repertoire of Delta-like 4 (DLL4) ligands with greatly enhanced affinity for multiple human Notch receptors.

1. Example 1: Directed Evolution Strategy for Screening High-Affinity Notch Ligands Delta-Like 4 (DLL4)

Figures 3A, 3B, 3C:
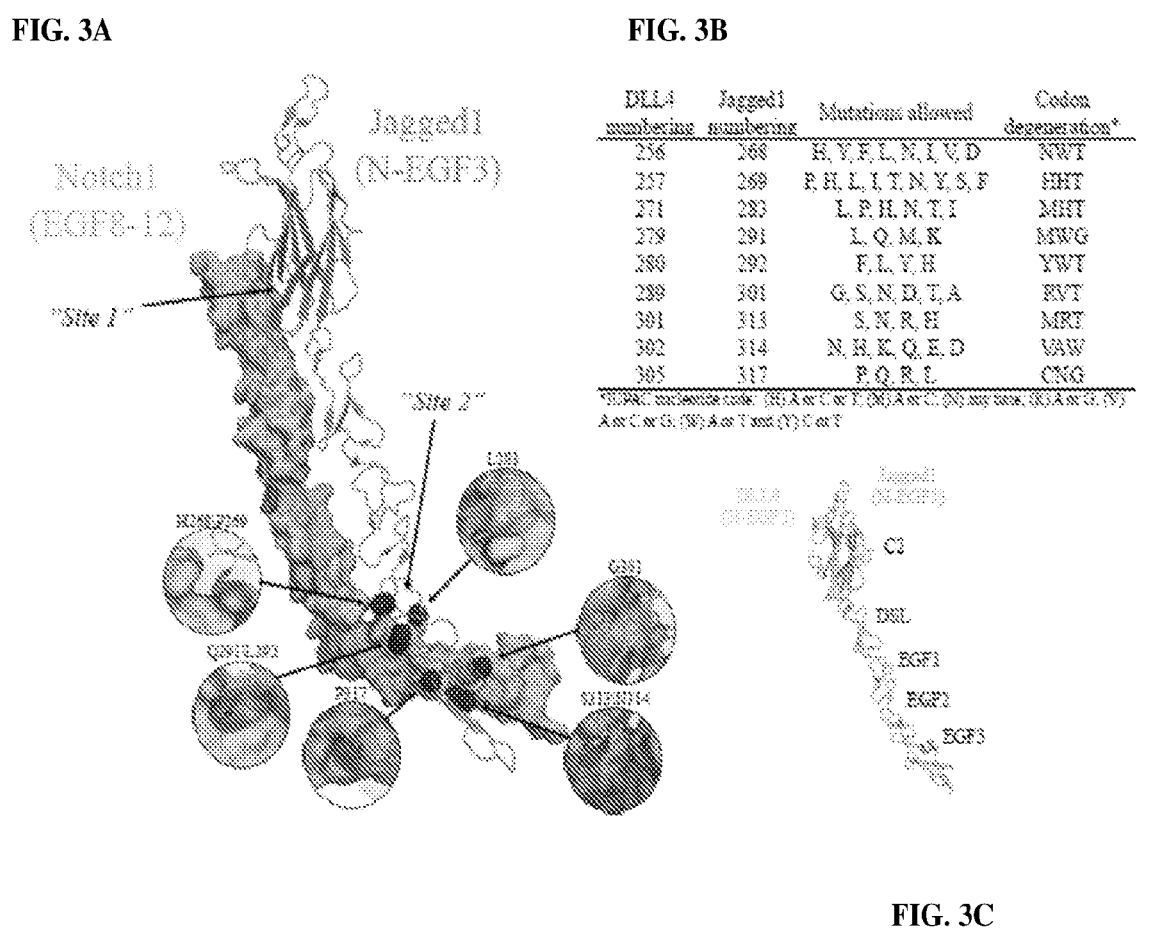

Based on the crystal structure of the protein complex Notch1-Jagged1 (PDB: 5UK5)2, putative hot-spot residues in the receptor-ligand interface were mapped to create new contacts in DLL4 similar to those of Jagged1 which were involved in a potential second binding site (FIG. 3A). With this information, mutant libraries containing degenerate oligonucleotides at 9 specific positions located at EGF2 and EGF3 of DLL4 were designed (FIG. 3B).

A mutant library was generated of about $8 \times 10^6$ variants of human DLL4, which was expressed by yeast surface display and subjected to iterative rounds of screening and selection through MACS and FACS by using human Notch 3 or Notch 1 as binding partners. In this process, the yeast expressing DLL4 ligands are incubated with tetramers or monomers of Notch and then sorted in magnetic columns. The high-affinity binders yielded after this selection are subjected to more stringent conditions to isolate the best binders (FIGS. 4A, 4B, 4C, and 4D).

2. Example 2: Construction of Chimeric DLL4 by Mutational Transfer

The improved variants obtained by directed evolution were combined with additional mutations found in former directed evolution campaigns using orthologous rat DLL4 ligands for affinity-maturation, E12 mutant3 (FIGS. 5A and 5B). The mutational transfer from rat to human yielded two new variants containing 10 and 11 final mutations located at two binding interfaces of Notch.

3. Example 3: Characterization of Binding Affinities by SPR

The final chimeric proteins were produced in insect cells, purified and assayed by Surface Plasmon Resonance (SPR) (FIGS. 6A and 6B), where Notch receptors are immobilized to a Streptavidin chip and then DLL4 is flowed at different concentrations. The combo mutants (N3a.5/N3a.8+E12) exhibited significantly improved binding affinities for Notch 1 and Notch 3, showing dissociation values (KD) in the low nanomolar range, whereas this value for the wild-type was found in the micromolar range. Additionally, we detected that the cross-reactivity of the new DLL4 ligands also was enhanced for Notch 2 and Notch 4, making these DLL4 variants valuable tools for promiscuous Notch engagement.

Binding affinities between DLL4 variants and Notch receptor subtypes were determined by surface plasmon resonance (SPR) (FIG. 7). Notch1 EGF domains 6-13, Notch2, EGF domains 6-13, or Notch 3 EGF domains 5-12 were immobilized on a sensor chip and various concentrations of DLL4 ligands were injected over the surface. A co-culture assay was used to monitor the inhibition of Notch signaling by DLL4.v3 (FIG. 8). A fluorescent Notch1 reporter cell line (CHO$^{N1}$) was co-cultured with 293T cells expressing wild-type human DLL4 (293T$^{DLL4}$) in 96-well plates to activate signaling. This value was normalized to 100% Notch1 activation. A reduction in Notch1 activation was observed upon the addition of increasing concentrations of DLL4.v3 (20 nM, 200 nM, 2000 nM) to the co-cultures.

4. Conclusion

We affinity-matured DLL4 using a structure-guided mutant library that varied 9 potential contact residues within the Notch-binding site. After performing several rounds of selection against Notch 1 and Notch 3, we isolated two variants that contain several mutations in the DLL4 EGF2 and EGF3 domains. Both human DLL4 variants were further modified to incorporate 5 additional mutations derived from a previously reported high-affinity rat DLL4 variant. The final chimeric proteins exhibited greatly increased binding relative to wild-type DLL4, with binding KD values decreasing from the micromolar range to the low nanomolar range. Additionally, we determined that the newly generated DLL4 ligands had enhanced affinity for Notch1-4, indicating that they have the potential to function as broadly reactive activators. In the future, we will assess the potential of these ultra-potent DLL4 variants in applications related to cancer therapy, T-cell stimulation, and stem cell differentiation.

E. References

Nowel, et al. Notch as a tumour suppressor. *Nat Rev Cancer,* 2017; 17(3):145-159.

Luca V C, et al. Notch-Jagged complex structure implicates a catch bond in tuning ligand sensitivity. *Science,* 2017; 355(6331):1320-1324.

Luca V C, et al. Structural basis for Notch1 engagement of Delta-like 4. *Science,* 2015; 347(6224): 847-885

F. Sequences
amino acid sequence for wildtype (WT) human
DLL4 starting at residue 27

SEQ ID NO: 1
```
SGVFQLQLQEFINERGVLASGRPCEPGCRTFFRVCLKHFQAVVSPGPCTF

GTVSTPVLGTNSFAVRDDSSGGGRNPLQLPFNFTWPGTFSLIIEAWHAPG

DDLRPEALPPDALISKIAIQGSLAVGQNWLLDEQTSTLTRLRYSYRVICS

DNYYGDNCSRLCKKRNDHFGHYVCQPDGNLSCLPGWTGEYCQQPICLSGC

HEQNGYCSKPAECLCRPGWQGRLCNECIPHNGCRHGTCSTPWQCTCDEGW

GGLFCDQDLNYCTHHSPCKNGATCSNSGQRSYTCTCRPGYTGVDCE
``` amino acid sequence for E12 human DLL4
starting at residue 27

SEQ ID NO: 2
```
SSVFQLQLQEFINERGVLASGRPCEPGCRTFFRVCLKHFQAVVSPGPCTF

GTVSTPVLGNSFAVRDDSSGGGRNPLQLPLNFTWPGTFSLIIEAWHAPGD

DLRPEALPPDALISKFAIQGSLAVGQNWLLDEQTSTLTRLRYSYRVICSD

NYYGDNCSRLCKKRNDYFGHYVCQPDGNPSCLPGWTGEYCQQPTCLSGCH

EQNGYCSKPAECLCRPGWQGRLCNECIPHNGCRHGTCSTPWQCTCDEGWG

GLFCDQDLNYCTHHSPCKNGATCSNSGQRSYTCTCRPGYTGVDCE
``` amino acid sequence for N3a.8_E12 human
DLL4 starting at residue 27

SEQ ID NO: 3
```
SSVFQLQLQEFINERGVLASGRPCEPGCRTFFRVCLKHFQAVVSPGPCTF

GTVSTPVLGNSFAVRDDSSGGGRNPLQLPLNFTWPGTFSLIIEAWHAPGD

DLRPEALPPDALISKFAIQGSLAVGQNWLLDEQTSTLTRLRYSYRVICSD

NYYGDNCSRLCKKRNDYFGHYVCQPDGNPSCLPGWTGEYCQQPICLSGCH

EQNGYCSKPAECLCRPGWQGRLCNECIPYPGCRHGTCSTPWQCLCDEGWG

GLYCDQDLNYCTHHSPCKNGATCHNSGPRSYTCTCRPGYTGVDCE
``` amino acid sequence for N3a.5_E12 human
DLL4 starting at residue 27

SEQ ID NO: 4
```
SSVFQLQLQEFINERGVLASGRPCEPGCRTFFRVCLKHFQAVVSPGPCTF

GTVSTPVLGNSFAVRDDSSGGGRNPLQLPLNFTWPGTFSLIIEAWHAPGD

DLRPEALPPDALISKFAIQGSLAVGQNWLLDEQTSTLTRLRYSYRVICSD

NYYGDNCSRLCKKRNDYFGHYVCQPDGNPSCLPGWTGEYCQQPICLSGCH

EQNGYCSKPAECLCRPGWQGRLCNECIPHPGCRHGTCSTPWQCLCDEGWG

GLYCDODLNYCTHHSPCKNGATCRNSGPRSYTCTCRPGYTGVDCE
```

---

What is claimed is:

1. An engineered DLL4 protein comprising a conservative amino acid substitution at a residue corresponding to residues 28, 107, 143, 194, and 206 as set forth in SEQ ID NO: 1 and further comprising at least one conservative amino acid substitution at residues 256, 257, 271, 280, 301, and 305 as set forth in SEQ ID NO: 1.

2. The engineered DLL4 protein of claim 1, wherein the substitution at residue 28 comprises a glycine to serine substitution (G28S).

3. The engineered DLL4 protein of claim 1, wherein the substitution at residue 107 comprises a phenylalanine to leucine substitution (F107L).

4. The engineered DLL4 protein of claim 1, wherein the substitution at residue 143 comprises an isoleucine to phenylalanine substitution (1143F).

5. The engineered DLL4 protein of claim 1, wherein the substitution at residue 194 comprises a histidine to tyrosine substitution (H194Y).

6. The engineered DLL4 protein of claim 1, wherein the substitution at residue 206 comprises a leucine to proline substitution (L206P).

7. The engineered DLL4 protein of claim 1, wherein the amino acid at residue 256 comprises a histidine, tyrosine, phenylalanine, leucine, asparagine, isoleucine, valine, or aspartic acid (H256, H256Y, H256F, H256L, H256N, H256I, H256V, or H256D).

8. The engineered DLL4 protein of claim 1, wherein the substitution at residue 256 comprises a histidine to tyrosine substitution (H256Y).

9. The engineered DLL4 protein of claim 1, wherein the amino acid at residue 257 comprises a proline, histidine, leucine, isoleucine, threonine, asparagine, tyrosine, serine, or phenylalanine (N257, N257P, N257H, N257L, N257I, N257T, N257Y, N257S, or N257F).

10. The engineered DLL4 protein of claim 1, wherein the substitution at residue 257 comprises an asparagine to proline substitution (N257P).

11. The engineered DLL4 protein of claim 1, wherein the amino acid at residue 271 comprises a leucine, proline, histidine, asparagine, threonine, or isoleucine (T271, T271L, T271P, T271H, T271N, or T271I).

12. The engineered DLL4 protein of claim 1, wherein the substitution at residue 271 comprises a threonine to leucine substitution (T271L).

13. The engineered DLL4 protein of claim 1, wherein the amino acid at residue 280 comprises a phenylalanine to leucine, tyrosine, or histidine substitution (F280Y, F280L, or F280H).

14. The engineered DLL4 protein of claim 1, wherein the amino acid at residue 301 comprises a serine, asparagine, arginine, or histidine (S301, S301H, S301N, or S301R).

15. The engineered DLL4 protein of claim 1, wherein the substitution at residue 301 comprises a serine to histidine substitution (S301H) or a serine to arginine substitution (S301R).

16. The engineered DLL4 protein of claim 1, wherein the amino acid at residue 305 comprises a glutamine to proline, arginine, or leucine substitution (Q305P, Q305R, or Q305L).

17. The engineered DLL4 protein of claim 1, wherein DLL4 protein comprises SEQ ID NO: 3 or SEQ ID NO: 4.

18. An antibody that specifically binds the engineered DLL4 proteins of claim 1.

19. A method of treating a Notch 1-3 related cancer in a subject comprising administering to the subject the engineered DLL4 proteins of claim 1.

20. A method of treating a Notch 1-3 related cancer in a subject comprising administering to the subject the antibody of claim 18.

* * * * *

SEQUENCE LISTING

<160> NUMBER OF SEQ ID NOS: 4

<210> SEQ ID NO 1
<211> LENGTH: 296
<212> TYPE: PRT
<213> ORGANISM: Homo sapiens

<400> SEQUENCE: 1

```
Ser Gly Val Phe Gln Leu Gln Leu Gln Glu Phe Ile Asn Glu Arg Gly
1               5                   10                  15
```

-continued

```
Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
            115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
            195                 200                 205

Lys Pro Ala Glu Cys Leu Cys Arg Pro Gly Trp Gln Gly Arg Leu Cys
    210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
            275                 280                 285

Gly Tyr Thr Gly Val Asp Cys Glu
    290                 295
```

<210> SEQ ID NO 2
<211> LENGTH: 295
<212> TYPE: PRT
<213> ORGANISM: Homo sapiens

<400> SEQUENCE: 2

```
Ser Ser Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Asn Ser Phe Ala Val
    50                  55                  60

Arg Asp Asp Ser Ser Gly Gly Gly Arg Asn Pro Leu Gln Leu Pro Leu
65                  70                  75                  80

Asn Phe Thr Trp Pro Gly Thr Phe Ser Leu Ile Ile Glu Ala Trp His
                85                  90                  95
```

-continued

```
Ala Pro Gly Asp Asp Leu Arg Pro Glu Ala Leu Pro Pro Asp Ala Leu
            100                 105                 110

Ile Ser Lys Phe Ala Ile Gln Gly Ser Leu Ala Val Gly Gln Asn Trp
            115                 120                 125

Leu Leu Asp Glu Gln Thr Ser Thr Leu Thr Arg Leu Arg Tyr Ser Tyr
            130                 135                 140

Arg Val Ile Cys Ser Asp Asn Tyr Tyr Gly Asp Asn Cys Ser Arg Leu
145                 150                 155                 160

Cys Lys Lys Arg Asn Asp Tyr Phe Gly His Tyr Val Cys Gln Pro Asp
                165                 170                 175

Gly Asn Pro Ser Cys Leu Pro Gly Trp Thr Gly Glu Tyr Cys Gln Gln
                180                 185                 190

Pro Ile Cys Leu Ser Gly Cys His Glu Gln Asn Gly Tyr Cys Ser Lys
                195                 200                 205

Pro Ala Glu Cys Leu Cys Arg Pro Gly Trp Gln Gly Arg Leu Cys Asn
            210                 215                 220

Glu Cys Ile Pro His Asn Gly Cys Arg His Gly Thr Cys Ser Thr Pro
225                 230                 235                 240

Trp Gln Cys Thr Cys Asp Glu Gly Trp Gly Gly Leu Phe Cys Asp Gln
                245                 250                 255

Asp Leu Asn Tyr Cys Thr His His Ser Pro Cys Lys Asn Gly Ala Thr
                260                 265                 270

Cys Ser Asn Ser Gly Gln Arg Ser Tyr Thr Cys Thr Cys Arg Pro Gly
                275                 280                 285

Tyr Thr Gly Val Asp Cys Glu
            290                 295

<210> SEQ ID NO 3
<211> LENGTH: 295
<212> TYPE: PRT
<213> ORGANISM: Homo sapiens

<400> SEQUENCE: 3

Ser Ser Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
            35                  40                  45

Thr Phe Gly Thr Val Ser Thr Pro Val Leu Gly Asn Ser Phe Ala Val
            50                  55                  60

Arg Asp Asp Ser Ser Gly Gly Gly Arg Asn Pro Leu Gln Leu Pro Leu
65                  70                  75                  80

Asn Phe Thr Trp Pro Gly Thr Phe Ser Leu Ile Ile Glu Ala Trp His
                85                  90                  95

Ala Pro Gly Asp Asp Leu Arg Pro Glu Ala Leu Pro Pro Asp Ala Leu
            100                 105                 110

Ile Ser Lys Phe Ala Ile Gln Gly Ser Leu Ala Val Gly Gln Asn Trp
            115                 120                 125

Leu Leu Asp Glu Gln Thr Ser Thr Leu Thr Arg Leu Arg Tyr Ser Tyr
            130                 135                 140

Arg Val Ile Cys Ser Asp Asn Tyr Tyr Gly Asp Asn Cys Ser Arg Leu
145                 150                 155                 160

Cys Lys Lys Arg Asn Asp Tyr Phe Gly His Tyr Val Cys Gln Pro Asp
```

-continued

```
                         165                 170                 175

Gly Asn Pro Ser Cys Leu Pro Gly Trp Thr Gly Glu Tyr Cys Gln Gln
                180                 185                 190

Pro Ile Cys Leu Ser Gly Cys His Glu Gln Asn Gly Tyr Cys Ser Lys
                195                 200                 205

Pro Ala Glu Cys Leu Cys Arg Pro Gly Trp Gln Gly Arg Leu Cys Asn
    210                 215                 220

Glu Cys Ile Pro Tyr Pro Gly Cys Arg His Gly Thr Cys Ser Thr Pro
225                 230                 235                 240

Trp Gln Cys Leu Cys Asp Glu Gly Trp Gly Gly Leu Tyr Cys Asp Gln
                245                 250                 255

Asp Leu Asn Tyr Cys Thr His His Ser Pro Cys Lys Asn Gly Ala Thr
                260                 265                 270

Cys His Asn Ser Gly Pro Arg Ser Tyr Thr Cys Thr Cys Arg Pro Gly
                275                 280                 285

Tyr Thr Gly Val Asp Cys Glu
    290                 295

<210> SEQ ID NO 4
<211> LENGTH: 295
<212> TYPE: PRT
<213> ORGANISM: Homo sapiens

<400> SEQUENCE: 4

Ser Ser Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
                20                  25                  30

Arg Val Cys Leu Lys His Phe Gln Ala Val Val Ser Pro Gly Pro Cys
                35                  40                  45

Thr Phe Gly Thr Val Ser Thr Pro Val Leu Gly Asn Ser Phe Ala Val
    50                  55                  60

Arg Asp Asp Ser Ser Gly Gly Gly Arg Asn Pro Leu Gln Leu Pro Leu
65                  70                  75                  80

Asn Phe Thr Trp Pro Gly Thr Phe Ser Leu Ile Ile Glu Ala Trp His
                85                  90                  95

Ala Pro Gly Asp Asp Leu Arg Pro Glu Ala Leu Pro Pro Asp Ala Leu
                100                 105                 110

Ile Ser Lys Phe Ala Ile Gln Gly Ser Leu Ala Val Gly Gln Asn Trp
                115                 120                 125

Leu Leu Asp Glu Gln Thr Ser Thr Leu Thr Arg Leu Arg Tyr Ser Tyr
                130                 135                 140

Arg Val Ile Cys Ser Asp Asn Tyr Tyr Gly Asp Asn Cys Ser Arg Leu
145                 150                 155                 160

Cys Lys Lys Arg Asn Asp Tyr Phe Gly His Tyr Val Cys Gln Pro Asp
                165                 170                 175

Gly Asn Pro Ser Cys Leu Pro Gly Trp Thr Gly Glu Tyr Cys Gln Gln
                180                 185                 190

Pro Ile Cys Leu Ser Gly Cys His Glu Gln Asn Gly Tyr Cys Ser Lys
                195                 200                 205

Pro Ala Glu Cys Leu Cys Arg Pro Gly Trp Gln Gly Arg Leu Cys Asn
    210                 215                 220

Glu Cys Ile Pro His Pro Gly Cys Arg His Gly Thr Cys Ser Thr Pro
225                 230                 235                 240
```

-continued

```
Trp Gln Cys Leu Cys Asp Glu Gly Trp Gly Gly Leu Tyr Cys Asp Gln
            245                 250                 255

Asp Leu Asn Tyr Cys Thr His His Ser Pro Cys Lys Asn Gly Ala Thr
            260                 265                 270

Cys Arg Asn Ser Gly Pro Arg Ser Tyr Thr Cys Thr Cys Arg Pro Gly
        275                 280                 285

Tyr Thr Gly Val Asp Cys Glu
    290                 295
```